(12) United States Patent
Banks

(10) Patent No.: US 6,789,271 B2
(45) Date of Patent: Sep. 14, 2004

(54) EYE PROTECTION

(75) Inventor: Gary Banks, Felden (GB)

(73) Assignee: World Suncare Products, Ltd., Hempstead (GB)

( * ) Notice: Subject to any disclaimer, the term of this patent is extended or adjusted under 35 U.S.C. 154(b) by 0 days.

(21) Appl. No.: 10/101,546

(22) Filed: Mar. 18, 2002

(65) Prior Publication Data

US 2003/0172444 A1 Sep. 18, 2003

(51) Int. Cl.$^7$ .................................................. A61F 9/02
(52) U.S. Cl. .................................. 2/426; 2/441; 2/443
(58) Field of Search ........................ 2/13, 12, 15, 428, 2/426, 429, 434, 441, 442, 443; 351/43, 41, 47, 110, 46, 44; 128/857, 858

(56) References Cited

U.S. PATENT DOCUMENTS

| | | | | |
|---|---|---|---|---|
| 2,511,329 A | * | 6/1950 | Craig ............................ | 351/47 |
| 2,844,994 A | * | 7/1958 | Filler ........................... | 351/49 |
| 3,020,552 A | * | 2/1962 | Coon ............................ | 2/15 |
| 3,122,962 A | * | 3/1964 | De Angelis ..................... | 2/15 |
| 3,440,662 A | * | 4/1969 | O'Shea ......................... | 2/15 |
| 4,056,853 A | * | 11/1977 | Bottazzini et al. .............. | 2/443 |
| 4,162,542 A | * | 7/1979 | Frank ........................... | 2/15 |
| 4,656,668 A | * | 4/1987 | Castrejon ...................... | 2/15 |
| 4,689,838 A | * | 9/1987 | Angermann et al. ........... | 2/441 |
| 4,701,962 A | * | 10/1987 | Simon .......................... | 2/15 |
| 4,790,031 A | * | 12/1988 | Duerer ......................... | 2/439 |
| 5,093,940 A | * | 3/1992 | Nishiyama ..................... | 2/441 |
| 5,307,523 A | * | 5/1994 | Lewis et al. ................... | 2/433 |
| 5,502,516 A | * | 3/1996 | Elterman ...................... | 351/47 |
| 5,764,333 A | * | 6/1998 | Somsel ......................... | 351/47 |
| 5,927,279 A | * | 7/1999 | Oviatt .......................... | 2/13 |
| 6,023,791 A | * | 2/2000 | Chiang ......................... | 2/441 |
| 6,092,243 A | * | 7/2000 | Wu et al. ...................... | 2/441 |
| 6,131,208 A | * | 10/2000 | Banks ........................... | 2/432 |

* cited by examiner

Primary Examiner—Gary L. Welch
(74) Attorney, Agent, or Firm—Woodard, Emhardt, Moriarty, McNett & Henry LLP

(57) ABSTRACT

An eye protection apparatus is disclosed that includes detachable dome-shaped eye protection portions.

24 Claims, 3 Drawing Sheets

EYE PROTECTION

BACKGROUND OF THE INVENTION

This invention relates to eye protection. In particular, it relates to protective eye wear, for protecting eyes against radiation, that can be used in a variety of environments.

The use of sun lamps and ultraviolet lamps for tanning skin has increased greatly over recent years. In addition to the traditional 'sunbed', where a user lies in a prone position on a platen beneath a sun-canopy, there is also tanning equipment that require a user to be in an upright position.

Conventionally, a user 20 (see FIG. 1) preparing for a tanning session using the 'prone' method would lie down on the platen and place an individual eye protector 21 over each eye before activating the lamp(s). Advantageously, these type of eye protectors cover the minimum area of facial skin during use.

When using the 'upright' method, a user cannot use the individual-type eye protectors since they will not remain in place over a user's eyes due to the position of the body. In this instance the type of protection goggles 22 as shown in FIG. 2 are required. Here, a user wears the goggles in much the same way as a swimmer wears swimming goggles; the eyepieces are interconnected via a nose bridge 23 and are fastened to an elastic headband 25 at fastening portions 24. These goggles do not slip from the wearers face, even when the wearer is in an upright position.

Since users of tanning equipment often use both of the methods described above, many of them are require to obtain both types of eye protectors; both the individual and the head-band fastening type of goggles.

An object of the present invention is to provide an improved eye protector.

SUMMARY OF THE INVENTION

According to an aspect of the present invention there is provided eye protection apparatus comprising eye protection goggles including detachable eye protection portions.

Preferably, the apparatus includes a means for securing the detachable portions to a frame portion of the goggles. Preferably, this provides a substantially light-tight attachment.

According to the present invention in a further aspect there is provided eye protection goggles including: a frame section comprising orbit portions adapted to surround a user's orbit, the orbit portions interconnected via a nose bridge; detachable eye portions adapted to filter ultraviolet radiation; and detachable attachment portions adapted to surround and secure to the frame section the eye portions.

The eye portions may be generally dome-shaped or otherwise shaped to have a hollow.

DESCRIPTION OF THE DRAWINGS

An embodiment of the invention will now be described, by way of example only, with reference to the accompanying schematic drawings, in which.

DESCRIPTION OF A PREFERRED EMBODIMENT OF THE INVENTION

Figure 1:
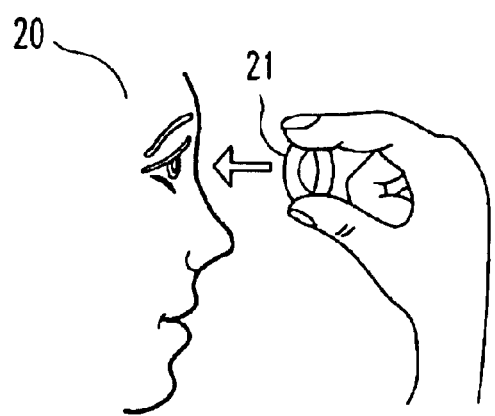
FIG. 1 shows a conventional individual eye protector.
Figure 2:
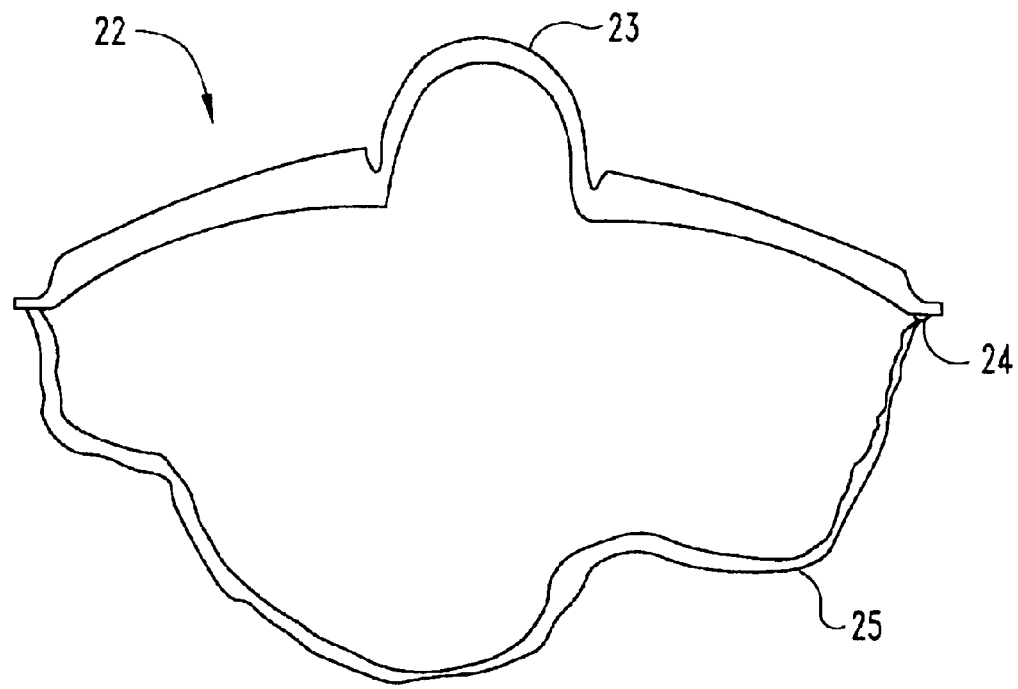
FIG. 2 shows schematically a pair of conventional eye goggles.
Figure 3:
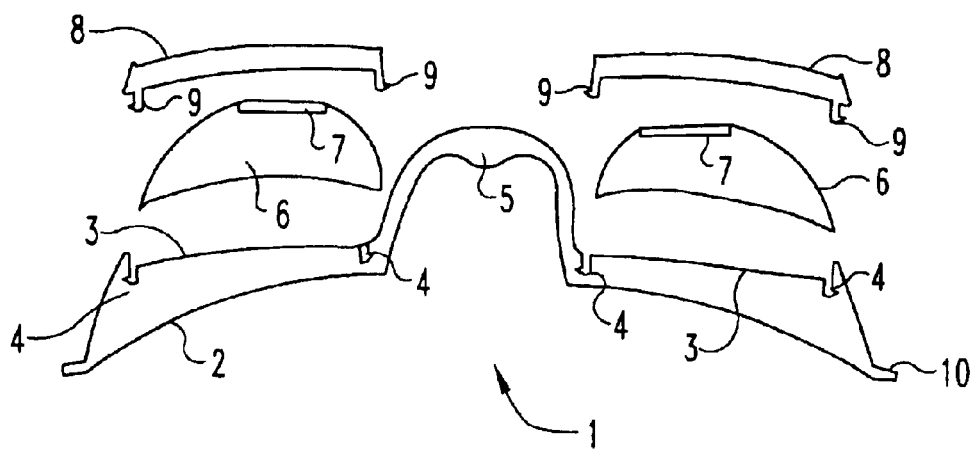
FIG. 3 shows an exploded view of a pair of eye protection goggles according to the present invention.
Figure 4:
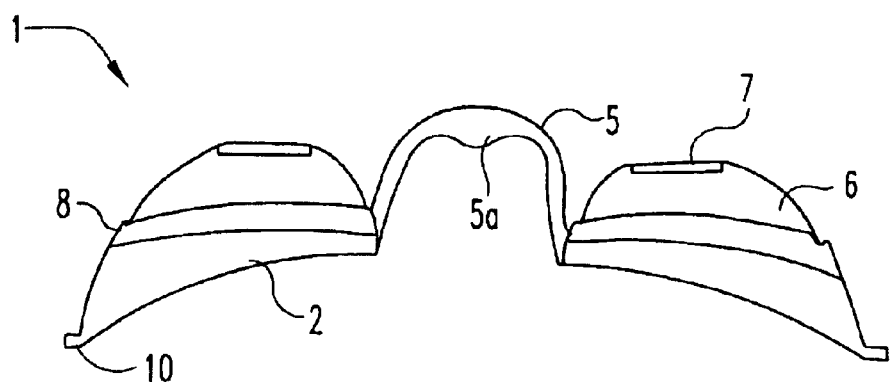
FIG. 4 shows an unexploded view of the eye protection goggles of FIG. 3.
Figure 5:
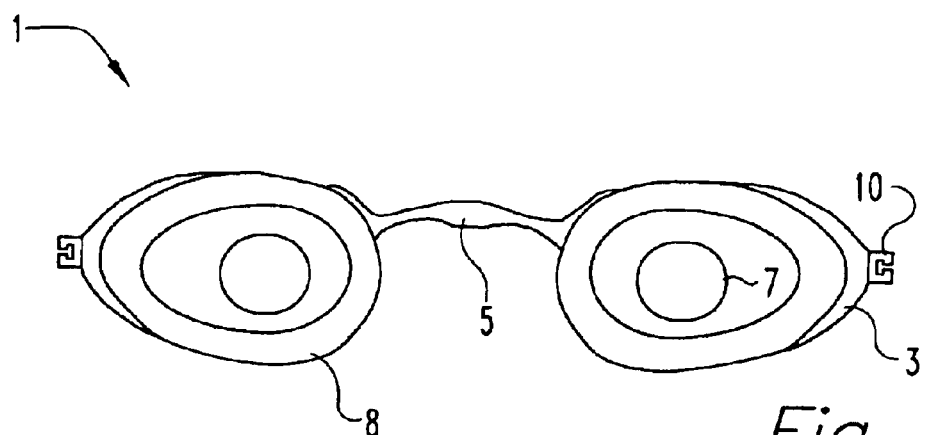
FIG. 5 shows a front view of the eye protection goggles show in FIG. 4.

Referring to FIGS. 3 to 5, a pair of eye protection goggles 1 includes a frame 2, eye protectors 6, and locking sleeves 8.

The frame 2 comprises two orbit portions 3 interconnected via a nose bridge 5. The nose bridge 5 may be rigid, flexible or a concertina-type linkage for example. The bridge preferably includes a widened central portion 5a, for strength. The eye protectors 6, which generally have an oval shaped base that abuts an orbit portion, are fabricated from a plastics material, preferably a rigid plastics material, for example ABS. The eye protector 6 includes a lens 7 of typically circular aperture. The lens is adapted to block both UVA and UVB light from impinging on the eyes of the wearer but may allow a degree of vision through it.

In order that the eye protectors 6 can be secured to the frame; the eye protection goggles include detachable locking sleeves 8. The sleeves 8 are adapted to enclose around the lower periphery of the eye protectors 6, and to releasably engage with respective orbit portions 3. Engagement is achieved via the mating of lugs 9 with reciprocal sockets 4 disposed on the orbit portions 3. The locking sleeves are dimensioned such that they can pass unhindered over the lens portion of the eye protectors 6, but cannot pass over the lower periphery of the eye protectors due to the increased circumference of the eye protectors. Also, the sleeves are of an adequate thickness to hold the eye protectors in abutment with the orbit portions without exerting more than necessary pressure, whilst also preventing the eye protectors from movement in any direction within the frame 2.

Alternatively, the sleeves may have an adhesive connection with the frame.

In alternative embodiments, the sleeves may be omitted entirely, and the eye protectors arranged to directly engage the frames, either by a mechanical fitting, or simply be adhesive fitting, for example.

Mating of the lugs 9 with the sockets 4 is achieved by a snap fit, force fit or any other such known method of releasably attaching these components. In alternative embodiments the mating may be achieved via a non-permanent adhesive layer disposed between the eye protectors and the orbit portions; in another embodiment the eye protectors are clipped or adhered onto the frame directly in one of a variety of know ways. Other methods of attaching a protector to a frame may be used whatever way, whatever method is used it will usually be useful to ensure that the attachment between the protectors and frames is light-tight.

Once the eye protectors 6 have been secured to the frame 2 via the locking sleeves 8, the goggles 1, as shown in FIG. 4, can be attached to a user's head. This is normally achieved by attaching an elasticated headband to the attachment lugs 10 located to the left and right periphery of the left and right eye protector respectively. Once in place, the headband can be passed over the user's head and worn in the usual manner.

FIG. 5 shows a front view of the eye protection goggles 1 with protectors secured in place.

Figure 6:
FIG. 6 shows a nose-bridge portion of a pair of goggles.

FIG. 6 shows a nose bridge portion 20 according to a further embodiment, which is generally concertinaed, to provide flexibility and wearability.

Figure 7:
FIG. 7 shows an alternative design of eye protectors.
Figure 8:
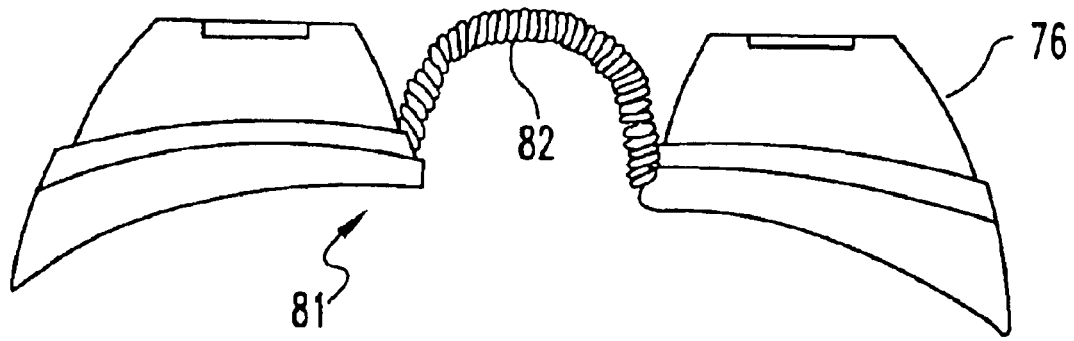
FIG. 8 shows a side view of a pair of goggles having the eye-protectors of FIG. 7.

FIG. 7 shows an alternative design of eye protector 76, having a generally flattened front portion 77 in which the lens is mounted. FIG. 8 shows a pair of goggles 81 incorporating such eye protectors. This pair includes a concertina-type nose bridge 82 but may of course have any other type of nose bridge.

What is claimed is:

1. Eye protection goggles comprising:

a frame portion; and eye protection portions detachably connected to the frame portion and adapted to filter ultraviolet radiation;

locking sleeves that detachably connect the eye protection portions to the frame portion, wherein each eye protection portion protrudes from an opening in a corresponding one of the locking sleeves, and wherein each locking sleeve includes a lug that engages a socket in the frame portion to detachably connect the eye protection portions to the frame portion.

2. The eye protection goggles of claim 1, wherein the eye protection portions are connected to the frame portion to provide a light-tight connection.

3. The eye protection goggles of claim 1, wherein the eye protection portions are dome-shaped.

4. The eye protection goggles of claim 1, wherein the eye protection portions block both UVA and UVB light from impinging on the eyes of the wearer but allow for vision therethrough.

5. The eye protection goggles of claim 1 further comprising a head attachment member connected to the frame portion, wherein the head attachment member holds the frame portion to the wearer.

6. The eye protection goggles of claim 1, wherein the eye protection portions include lenses.

7. Eye protection goggles comprising:

a frame portion; and eye protection portions detachably connected to the frame portion and adapted to filter ultraviolet radiation, wherein each eye protection portion includes a base and a protruding portion; and locking sleeves that detachably connect the eye protection portions to the frame portion, wherein each eye protection portion protrudes from an opening in a corresponding one of the locking sleeves, and wherein the base is larger than and the protruding portion is smaller than an opening in a corresponding one of the locking sleeves.

8. The eye protection goggles of claim 7, wherein the eye protection portions are dome-shaped.

9. The eye protection goggles of claim 7, wherein the eye protection portions are connected to the frame portion to provide a light-tight connection.

10. The eye protection goggles of claim 7, wherein the eye protection portions block both UVA and UVB light from impinging on the eyes of the wearer but allow for vision therethrough.

11. The eye protection goggles of claim 7, further comprising a head attachment member connected to the frame portion, wherein the head attachment member holds the frame portion to the wearer.

12. The eye protection goggles of claim 7, wherein the eye protection portions include lenses.

13. Eye protection goggles comprising:

a frame section comprising orbit portions adapted to surround a user's orbit, the orbit portions being interconnected via a nose bridge;

eye portions detachably connected to the frame section and adapted to filter ultraviolet radiation; and attachment portions adapted to surround and detachably secure the eye portions to the frame section, wherein each eye portion protrudes from an opening in a corresponding one of the attachment portions: and wherein each attachment portion includes a lug that engages a socket in the frame section to detachably connect a corresponding one of the eye portions to the frame section.

14. The eye protection goggles of claim 13, wherein the eye portions are connected to the frame section to provide a light-tight connection.

15. The eye protection goggles of claim 13, wherein the eye portions are dome-shaped.

16. The eye protection goggles of claim 13, wherein the eye portions block both UVA and UVB light from impinging on the eyes of the wearer but allow for vision therethrough.

17. The eye protection goggles of claim 13 further comprising a head attachment member connected to the frame section, wherein the head attachment member holds the frame section to the wearer.

18. The eye protection goggles of claim 13, wherein each eye portion is formed coextensive in the opening in a corresponding one of the attachment portions.

19. Eye protection goggles comprising:

a frame section comprising orbit portions adapted to surround a user's orbit, the orbit portions being interconnected via a nose bridge;

eye portions detachably connected to the frame section and adapted to filter ultraviolet radiation, wherein each eye portion includes a base and a protruding portion; and attachment portions adapted to surround and detachably secure the eye portions to the frame section, wherein each eye portion protrudes from an opening in a corresponding one of the attachment portion, and wherein the base is larger than and the protruding portion is smaller than an opening in a corresponding one of the attachment portions.

20. The eye protection goggles of claim 19, wherein the eye portions are dome-shaped.

21. The eye protection goggles of claim 19, wherein the eye portions are connected to the frame section to provide a light-tight connection.

22. The eye protection goggles of claim 19, wherein the eye portions block both UVA and UVB light from impinging on the eyes of the wearer but allow for vision therethrough.

23. The eye protection goggles of claim 19 further comprising a head attachment member connected to the frame section, wherein the head attachment member holds the frame section to the wearer.

24. The eye protection goggles of claim 19, wherein each eye portion is formed coextensive in the opening in a corresponding one of the attachment portions.

* * * * *